(12) United States Patent
McDonough et al.

(10) Patent No.: US 8,309,134 B2
(45) Date of Patent: Nov. 13, 2012

(54) MODIFIED CALCIUM PHOSPHATE NANOPARTICLE FORMATION

(75) Inventors: Joseph A McDonough, Helotes, TX (US); Hong Dixon, Helotes, TX (US); Maria Lucy Kimmel, San Antonio, TX (US); Larry Allen Cabell, San Antonio, TX (US); Stephen T. Wellinghoff, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 685 days.

(21) Appl. No.: 12/245,450

(22) Filed: Oct. 3, 2008

(65) Prior Publication Data
US 2010/0086601 A1 Apr. 8, 2010

(51) Int. Cl.
- A61K 9/51 (2006.01)
- A61K 31/5517 (2006.01)
- A61K 9/14 (2006.01)

(52) U.S. Cl. .................. 424/489; 424/490; 514/220
(58) Field of Classification Search .................. 424/489, 424/490; 514/220
See application file for complete search history.

(56) References Cited

U.S. PATENT DOCUMENTS

| | | | |
|---|---|---|---|
| 2,305,947 A | 8/1942 | Armstrong et al. |
| 2,305,917 A | 12/1942 | Armstrong |
| 2,816,113 A | 12/1957 | Wilson |
| 3,135,761 A | 6/1964 | Hackley et al. |
| 3,137,702 A | 6/1964 | Luttringhaus |
| 3,629,425 A | 12/1971 | Hussain |
| 3,929,813 A | 12/1975 | Higuchi et al. |
| 4,128,651 A | 12/1978 | Hagedorn |
| 4,305,947 A | 12/1981 | Bartner |
| 4,540,602 A | 9/1985 | Motoyama et al. |
| 4,705,777 A | 11/1987 | Lehrer et al. |
| 4,880,610 A | 11/1989 | Constantz |
| 5,130,438 A | 7/1992 | Hsiao et al. |
| 5,145,684 A | 9/1992 | Liversidge et al. |
| 5,298,504 A | 3/1994 | Sommer et al. |
| 5,589,167 A | 12/1996 | Cleland |
| 5,662,883 A | 9/1997 | Bagchi et al. |
| 5,716,642 A | 2/1998 | Bagchi et al. |
| 5,770,181 A | 6/1998 | Kirkland |

(Continued)

FOREIGN PATENT DOCUMENTS
EP 1319400 6/2003
(Continued)

OTHER PUBLICATIONS

Radic, et al., "Evaluation of HI-6 oxime: potential use in protection of human acetylcholinesterase inhibited by antineoplastic drug irinotecan and its cyto/genotoxicity in vitro," Acta Biochimica Polonica vol. 54 No. 03/2007, 583-593, Aug. 23, 2007.

(Continued)

*Primary Examiner* — Aradhana Sasan
(74) *Attorney, Agent, or Firm* — Grossman Tucker et al (57) ABSTRACT

The present disclosure relates to non-aggregating nanoparticles and their associated methods of preparation. The nanoparticles may have a surface and a size range of 1 nm to 999 nm, along with a zeta potential of −50 to 50 millivolts. A polycation and/or polyanion may be disposed on the nanoparticle surface. In addition, an active ingredient may be encapsulated within the nanoparticles or associated with the polycation or polyanion on the nanoparticle surface.

26 Claims, 8 Drawing Sheets

U.S. PATENT DOCUMENTS

| | | | |
|---|---|---|---|
| 5,902,816 A | 5/1999 | Viner | |
| 5,929,093 A | 7/1999 | Pang et al. | |
| 6,007,845 A | 12/1999 | Domb et al. | |
| 6,117,454 A | 9/2000 | Kreuter et al. | |
| 6,355,271 B1 | 3/2002 | Bell et al. | |
| 6,395,029 B1 | 5/2002 | Levy et al. | |
| 6,656,505 B2 | 12/2003 | Kundu et al. | |
| 6,815,543 B1 | 11/2004 | Bernardelli | |
| 6,861,068 B2 | 3/2005 | Ng et al. | |
| 6,881,745 B2 | 4/2005 | Hayes et al. | |
| 7,037,528 B2 | 5/2006 | Kipp et al. | |
| 7,081,161 B2 | 7/2006 | Genge et al. | |
| 7,282,194 B2 | 10/2007 | Sung et al. | |
| 7,300,670 B2 | 11/2007 | Venus et al. | |
| 7,387,792 B2 | 6/2008 | Hirsh et al. | |
| 7,390,384 B2 | 6/2008 | Fang et al. | |
| 7,897,176 B2 * | 3/2011 | Kataoka et al. | 424/489 |
| 2003/0073619 A1 * | 4/2003 | Mahato et al. | 514/8 |
| 2004/0022820 A1 | 2/2004 | Anderson | |
| 2004/0256749 A1 | 12/2004 | Chaubal et al. | |
| 2004/0266890 A1 | 12/2004 | Kipp et al. | |
| 2005/0106257 A1 | 5/2005 | Albayrak | |
| 2005/0113489 A1 * | 5/2005 | Baran et al. | 523/300 |
| 2005/0118108 A1 | 6/2005 | Cowan et al. | |
| 2005/0220888 A1 | 10/2005 | Putcha et al. | |
| 2006/0063662 A1 | 3/2006 | Hata et al. | |
| 2006/0183777 A1 | 8/2006 | Huang et al. | |
| 2006/0216353 A1 | 9/2006 | Liversidge et al. | |
| 2007/0093518 A1 | 4/2007 | Wetherell et al. | |
| 2007/0134339 A1 | 6/2007 | Jenkins et al. | |
| 2007/0190160 A1 * | 8/2007 | Turos et al. | 424/490 |
| 2008/0145439 A1 | 6/2008 | Lobl et al. | |
| 2008/0241256 A1 * | 10/2008 | Kuhn | 424/489 |
| 2009/0263491 A1 | 10/2009 | Kreuter et al. | |
| 2009/0304720 A1 | 12/2009 | Kreuter et al. | |

FOREIGN PATENT DOCUMENTS

| | | |
|---|---|---|
| WO | 9814587 | 4/1998 |
| WO | 9841188 | 9/1998 |
| WO | 0163362 | 8/2001 |
| WO | 2002032402 | 4/2002 |
| WO | 2004073033 | 8/2004 |
| WO | 2005123581 | 12/2005 |
| WO | 2007/001355 A2 | 1/2007 |
| WO | 2007/084460 A2 | 7/2007 |
| WO | 2009114298 | 9/2009 |

OTHER PUBLICATIONS

Stojiljkovic, et al., "Pryidinum Oximes: Rationale for their Selection as casual Antidotes against Organophosphate Poisonings and current solutions for auto-injectors," Arh Hig Toksikol 2006, 57:435-443.

Gelperina, et al., "Drug delivery to the brain using surfactant-coated poly(lactide-co-glycolide) nanoparticles: Influence of the formulation parameters," European Journal of Pharmaceutics and Biopharmaceutics (2009) doi:10.1016/j.ejpb.2009.09.003.

Kurakhmaeva, et al, "Brain targeting of nerve growth factor using poly(butyl cyanoacrylate) nanoparticles," Journal of Drug Targeting, 2009; 17(8): 564-574.

Hekmatara, et al., "Efficient systemic therapy of rat glioblastoma by nanoparticle-bound doxorubicin is due to antiangiogenic effects," Clinical Neuropathology, vol. 28—No. 3/2009 (153-164).

Zensi, et al., "Albumin nanoparticles targeted with Apo E enter the CNS by transcytosis and are delivered to neurones," Journal of Controlled Release 137 (2009) 78-86.

Ulbrich, et al., "Transferrin- and transferrin-receptor-antibody-modified nanoparticles enable drug delivery across the blood-brain barrier (BBB)," European Journal of Pharmaceutics and Biopharmaceutics 71 (2009) 251-256.

Pereverzeva, et al., "Intravenous tolerance of a nanoparticle-based formulation of doxorubicin in healthy rats," Toxicology Letters 178 (2008) 9-19.

Kreuter, et al., "Use of nanoparticles for cerebral cancer," Tumori: 9-4: 271-277, 2008.

Kreuter, "Nanoparticles—a historical perspective," International Journal of Pharmaceutics 331 (2007) 1-10.

Petri, et al., "Mechanism of Action and Surfactant Influence During Chemotherapy of Brain Tumour Using Doxorubicin-Loaded Poly(butyl Cyanoacrylate) Nanoparticles," NSTI-Nanotech 2007, vol. 2, 2007, p. 386-389.

Ambruosi, et al., "Influence of surfactants, polymer and doxorubicin loading on the anti-tumour effect of poly(butyl cyanoacrylate) nanoparticles in a rat glioma model," Journal of Microencapsulation, Aug. 2006; 23(5): 582-592.

Ambruosi, et al., "Biodistribution of polysorbate 80-coated doxorubicin-loaded [14C]-poly(butyl cyanoacrylate) nanoparticles after intravenous administration to glioblastoma-bearing rats," Journal of Drug Testing, Feb. 2006; 14(2): 97-105.

Ambruosi, et al., "Body distribution of polysorbate-80 and doxorubicin-loaded [14C]-poly(butyl cyanoacrylate) nanoparticles after i.v. administration in rats," Journal of Drug Targeting, Dec. 2005; 13(10): 535-542.

Schuller et al., "Degradation of microvascular brain endothelial cell β-catenin after co-culture with activated neutrophils from patients undergoing cardiac surgery with prolonged cardiopulmonary bypass," Biochemical and Biophysical Research Communications 329 (2005) 616-623.

Kreuter, "Application of nanoparticles for the delivery of drugs to the brain," International Congress Series 1277 (2005) 85-94.

Kreuter, "Influence of the Surface Properties on Nanoparticle-Mediated Transport of Drugs to the Brain," Journal of Nanoscience and Nanotechnology, 2004, vol. 4, No. 5; p. 484-488.

Kreuter, "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles," Pharmaceutical Research, vol. 20, No. 3, Mar. 2003; p. 409-416.

Kreuter, "Transport of Drugs Across the Blood-Brain Barrier by Nanoparticles," Curr. Med. Chem.—Central Nervous System Agents, 2002, 2, 241-249.

Kreuter, et al."Apolipoprotein-medicated Transport of Nanoparticle-bound Drugs Across the Blood-Brain Barrier," Journal of Drug Testing, 2002 vol. 10 (4), pp. 317-325.

Gelperina, et al., "Toxicological studies of doxorubicin bound to polysorbate 80-coated poly(butyl cyanoacrykate) nanoparticles in healthy rats and rats with intracranial glioblastoma," Toxicology Letters 126 (2002) 131-141.

Kreuter, "Nanoparticulate systems for brain delivery of drugs," Advanced Drug Delivery Reviews 47 (2001) 65-81.

Ramge, et al., "Polysorbate-80 coating enhances uptake of polybutylcyanoacrylate (PBCA)-nanoparticles by human and bovine primary brain capillary endothelial cells," European Journal of Neuroscience, vol. 12, pp. 1931-1940 (2000).

Ramge, et al., "Circadian Phase-dependent Antinociceptive Reaction in Mice and the Tail-flick Test after Intravenous Injection of Dalargin-Loaded Nanoparticles," Chronobiology International, 16(6), 767-777 (1999).

Balali-Mood MD PHD, et al., "Neurotoxic Disorders of Organophosphorous Compounds and Their Managements," Arch Iranian Med 2008; 11 (1): 65-89.

Kuca, et al., "Preparation of Oxime HI-6 (Dichloride and Dimethanesulphonate)—Antidote against Nerve Agents," Defense Science Journal, vol. 58, No. 3, May 2008, pp. 399-404.

Antonijevic et al., "Unequal Efficacy of Pyridinium Oximes in Acute Organophosphate Poisoning," Clinical Medicine & Research, vol. 5, No. 1:71-82, 2007.

Kuca, et al., "In Vitro Reactivation Potency of Acetylcholinesterase Reactivators—K074 and K075—to Reactivate Tabun-inhibited Human Brain Cholinesterases," Neurotoxicity Research, 2007, vol. 11(2), pp. 101-106.

Chemistry and Industry; Applied Chemistry; Nigel Freestone; Nov. 7, 2005 (4 pgs).

Chemistry and Industry; New Drug Delivery Systems; Alexander T. Florence; Dec. 20, 1993 (7 pgs).

Advanstar Communications, Inc.; Pharmaceutical Technology; Vivek Kharb; Meenakshi Bhatia; Harish Dureja; Deepak Kaushik; Feb. 1, 2006 (11 pgs).

Advanstar Communications, Inc.; Pharmaceutical Technology Europe; Magdalene Radtke; Eliana B. Souto; Rainer H. Muller; Apr. 1, 2005 (4 pgs).
Dennison, et al. "Corticosteroids in rheumatoid arthritis," British Medical Journal vol. 316, pp. 789-790 (1998).
Kenalog® Creams Triamcinolone Acetonide Cream USPO.025%, 0.1 %,0.5% (Online) http://dari1ymed.n1m.nih.gOY1dai1ymed/fda/fdaDrugXsl.cfm?id=1872&type=display; retrieved Jun. 21, 2008 (8 pages).
D. Farcasiu, et al. "Evaluation of hydrogen bonding by C-13NMR" Catalysis Letters 31 (1995) 351-358.
International Search Report and Written Opinion of the ISA issued in PCT/US09/35539 dated Jul. 17, 2009 (8 pgs).
International Search Report and Written Opinion of the ISA issued in PCT/US09/52457 dated Oct. 6, 2009 (9 pgs).
Luo et al, "An in Vitro Comparative Study on the Reactivation of Nerve Agent-Inhibited Guinea Pig and Human Acetylcholinesterases by Oximes"; Biochemistry 2007, 46, pp. 11771-11779.
Garcia et al, "Sensitive and Rapid Blood and Tissue HPLC Oxime Assay and Pharmacokinetics of MMB-4 in Guinea Pigs and African Green Monkeys"; Walter Reed Army Institute of Research, Nov. 1, 2006, (8 pgs).
U.S. Office Action dated Dec. 9, 2010 issued in related U.S. Appl. No. 11/555,995.
Digiovanni, Jr., M.D., Cleto, Domestic Terrorism With Chemical or Biological Agents: Psychiatric Aspects, Am J Psychiatry, Oct. 1999, pp. 1500-1505, vol. 156:10.
D'Mello, G.D., Behavioural Toxicity of Anticholinesterases in Humans and Animals—A Review, Human & Experimental Toxicology, 1993, pp. 3-7, vol. 12.
Eyer, et al., Oximes—Chapter 15, Chemical Warfare Agents: Toxicology and Treatment, 2007, pp. 305-329, 2nd Edition.
Jager, et al., Toxicity of Diacetyl Monoxime and of Pyridine-2-Aldoxime Methiodide in Man, Bull John Hopkins Hosp., 1958, pp. 203-211, vol. 102.
Jamal, Goran A., Long term neurotoxic effects of organophosphate compounds, Adverse Drug React. Toxicol. Rev, 1995, pp. 85-99, vol. 14(2).
Marrs et al., Chemical Warfare Agents: Toxicology and Treatment Second Edition, 2007, pp. all. Table of contents attached electronically, physical book is cited and supplied in U.S. Appl. 12/702,095 which was mailed to USPTO Oct. 8, 2010.
McDonough, et al., Behavioral Correlates of Soman-Induced Neuropathology: Deficits in DRL Acquisition, Neurobehavioral Toxicology and Teratology, 1986, pp. 179-187, vol. 8.
U.S. Office Action dated Jun. 25, 2008 issued in U.S. Appl. No. 11/555,995, 23 pages.
U.S. Office Action dated Nov. 28, 2008 issued in U.S. Appl. No. 11/555,995, 8 pages.
International Search Report and Written Opinion dated Nov. 23, 2009 issued in PCT Patent Application No. PCT US09/59386, 12 pages.
Praetorius, et al., "Engineered Nanoparticles in Cancer Therapy," Recent Patents on Drug Delivery & Formation 2007,vol. 1 No. 1, pp. 37-51.
Biosante Pharmaceuticals, "Hormone Therapy—A Multi-Billion Dollar Market," Investor Fact Sheet Sep. 2007; www.biosantepharma.com; (2 pages).
T.Welzel, et al., "Transfection of Cells With Custom-made Calcium Phosphate Nanoparticles Coated With DNA"; The Royal Society of Chemistry 2004; J. Mater. Chem. 2004, 14, pp. 2213-2217.
S. Bisht, et al., "pDNA Loaded Calcium Phosphate Nanoparticles: Highly Efficient Non-Viral Vector for Gene Delivery"; International Journal of Pharmaceutics 288 (2005), pp. 157-168.
T.Liu, et al., "Calcium Phosphate Nanoparticles As a Novel Nonviral Vector for Efficient Transfection of DNA in Cancer Gene Therapy"; Cancer Biotherapy & Radiopharmaceuticls, vol. 20, No. 2, 2005, pp. 141-150.
A. Brioschi, et al, "Solid Lipid Nanoparticles: Could They Help . . . "; Neurological Research 2007, vol. 29, Apr. 2007; pp. 324-330.
M. Nahar, et al, "Functional Polymeric Nanoparticles: An Efficient . . . "; Critical Reviews™ in Therapeutic Drug Carrier Systems, 23(4):259-318 (2006); Begell House Inc., http://begellhouse.com; downloaded Sep. 18, 2009 from IP 129.162.1.41 by Celia Frausto.
U.S. Office Action dated Jun. 22, 2011 issued in related U.S. Appl. No. 12/047,988.
U.S. Office Action dated Aug. 15, 2011 issued in related U.S. Appl. No. 11/555,995.
Alyautdin, et al, "Drug delivery to brain by nanoparticles," (2003) eksperimental'naya i Klinicheskaya Farmakologiya, 66 (2), pp. 65-68. English language Abstract can be found on p. 68, final paragraph.
Luo, et al., "Development of a broad-spectrum Oxime for the treatment of nerve agent toxicity," Conference paper, Division of Biochemistry, Walter Reed Army Institute of Research, Silver Spring, MD 20910, Report Date: Nov. 2006 Report No. A376184. Available at http://www.dtic.mil/cgi-bin/GetTRDoc?Location=U2&doc=GetTRDoc.pdf&AD=ADA481673, retrieved on Mar. 9, 2011.
U.S. Office Action dated May 25, 2011 issued in related U.S. Appl. No. 12/192,400.
Munavalli, et al; Preparation and Properties of Methylenebispyridinium Derivatives; Heterocycles 1986, vol. 24. No. 7; pp. 1883-1892.
Giulian et al, "Short Communication", Optical and Quantum Electronics, vol. 9, pp. 263-264; 1977.
Patani et al, "Bioisosterism: A Rational Approach in Drug Design", (Chemical Reviews, vol. 96, No. 8, pp. 3147-3176; 1996.
U.S. Office Action dated Nov. 1, 2011 issued in related U.S. Appl. No. 11/555,995.
European Supplementary Search Report—mailing date Sep. 27, 2011, issued in related European Appln. No. 09718843.7.
Sevelova et al, "Antidotal Treatment of GF-agent intoxication in mice with bispyridinium Oximes", Toxicology, vol. 207, No. 1, pp. 1-6, 2005.
Aurbek et al, "Analysis of Inhibition, Reactivation and Aging Kinetics of Highly Toxic Organophosphorus Compounds with Human and Pig Acetylcholinesterase", Toxicology, vol. 224, No. 1-2. pp. 91-99, 2006.
Office Action dated Dec. 29, 2011 issued in related U.S. Appl. No. 12/047,988.
Wu, et al., "Blood-Brain Barrier Transport of Reduced Folic Acid," Pharm Res. Mar. 1999;16(3):415-9.
Office Action dated Jan. 26, 2012 issued in related U.S. Appl. No. 12/192,400.
Office Action dated Jan. 5, 2012 issued in related U.S. Appl. No. 12/702,095.
European Search Report dated Oct. 31, 2011 issued in related European Patent Application No. 09807064.2.
Bagryanskaya, et al., "Study of alkaloids from the flora of the Siberian and Altai regions. 6.* Crystal and molecular structure of songorine Z-oxime," Russian Chemical Bulletin, International Edition, vol. 50, No. 11, pp. 2092-2094, Nov. 2001.
Gao, et al., "Influence of particle size on transport of methotrexate across blood brain barrier by polysorbate 80-coated polybutylcyanoacrylate nanoparticles," International Journal of Pharmaceutics 310 (2006) 213-219.
Hobbiger, et al., "Reactivation of Phosphorylated Acetocholinesterases by Pyridinium Aldoximes and Related Compounds," Biochem J. May 1960; 75(2): 363-372.
Kuca, et al., "Effective bisquaternary reactivators of tabun-inhibited AChE," J. Appl. ToxiCol. 2005; 25: 491-495.
Liu, et al., "Biologically active core/shell nanoparticles self-assembled from cholesterol-terminated PEG-TAT for drug delivery across the blood-brain barrier," Biomaterials 29 (2008) 1509-1517.
Macauley, et al., Chromatographic separation and NMR characterization of the isomers of MMB-4 a bis-(pyridiniumaldoxime), Journal of Pharmaceutical and Biomedical Analysis 49 (2009) 889-894.
Thiermann, "HI 6 dimethanesulfonate has better dissolution properties than HI 6 dichloride for application in dry/wet autoinjectors," International Journal of Pharmaceutics vol. 137, Issue 2, Jun. 28, 1996, pp. 167-176.

* cited by examiner

MODIFIED CALCIUM PHOSPHATE NANOPARTICLE FORMATION

Government Rights Clause

This invention was made with United States Government support under DHHS Grant No. 5U19AI070202-02 PI Name: RAMRATNAM, BHARAT awarded by the National Institutes of Health/Department of Health and Human Services. The Government has certain rights in this invention.

FIELD OF THE INVENTION

The present invention relates to charged nanoparticles which may be formed and associated with various molecules, such as drugs, biological molecules, peptides, proteins, DNAs, RNAs, etc. The nanoparticles may specifically be developed with a desired zeta potential which may then be used to regulate particle agglomeration.

BACKGROUND

Nanotechnology focuses on the development of new materials, devices and systems that typically involves the formation of particles on the nanometer length scale. To date, a number of techniques have been developed, e.g. mechanical grinding and the formation of particles of a desired size, as well as certain chemical techniques that may rely upon controlled precipitation from a given liquid medium. Relatively intense research into nanotechnology has recently led to numerous potential applications, such as the formation of particles engineered to carry a variety of substances in a controlled and targeted manner for drug delivery. For example, nanoparticles may be relied upon to prevent degradation of a carried load and protect transported substances from contact with healthy tissue thereby reducing peripheral effects and increasing the relative amount of load reaching the desired tissue.

SUMMARY

In a first exemplary embodiment, the present disclosure relates to a method for preparing non-aggregating nanoparticles comprising mixing a solution of a calcium salt with a salt of phosphoric acid and adding an active ingredient to one of said calcium salt solution or phosphoric acid salt solution. This may then be followed by adjusting the pH to a level of greater than 7.0 and less than or equal to 10.0 and forming calcium phosphate nanoparticles and adding a polycation and/or polyanion and terminating the formation of said nanoparticles. The active ingredient may then be encapsulated in the nanoparticles, which nanoparticles may have a zeta potential of −50 to 50 millivolts (mV).

In another exemplary embodiment, the present disclosure relates to a method for preparing non-aggregating nanoparticles comprising mixing a solution of a calcium salt with a salt of phosphoric acid and adding a polycation and/or polyanion. This may then be followed by adjusting the pH to a level of greater than 7.0 and less than or equal to 10.0 and forming calcium phosphate nanoparticles and adding a polycation and/or polyanion to terminate the nanoparticle formation. This may then be followed by adding an active ingredient to the nanoparticles wherein the active ingredient is associated with the nanoparticle surface via a secondary bonding interaction (a bonding interaction other than a covalent bond).

In a still further exemplary embodiment, the present disclosure relates to a composition comprising non-aggregating nanoparticles having a surface and a size range of 1 nm to 999 nm, said nanoparticles having a zeta potential of −50 to 50 millivolts. A polycation and/or polyanion may then be positioned on the surface of the nanoparticles and an active ingredient may be encapsulated within and/or associated with the polycation or polyanion on the nanoparticle surface.

DETAILED DESCRIPTION

The present disclosure is directed at nanoparticles, which may be understood as one or more particles that are less than one micron (1.0 μm) in its largest dimension, and which, as explained more fully below, are generally non-aggregating. Accordingly, the nanoparticles herein may have a largest size dimension of 1 nm to 999 nm, including all values and increments therein, such as between 1-900 nm, 1-800 nm, 1-700 nm, etc., in 1 nm increments. Furthermore, the nanoparticles herein may specifically have a largest size dimension of 50-400 nm, or 100-300 nm, or 190-210 nm, including all values and increments therein in 1 nm increments. As may be appreciated, by regulating the nanoparticle size in such manner, the generally non-aggregating characteristics reported herein may be optimized for a given application.

Figure 1:
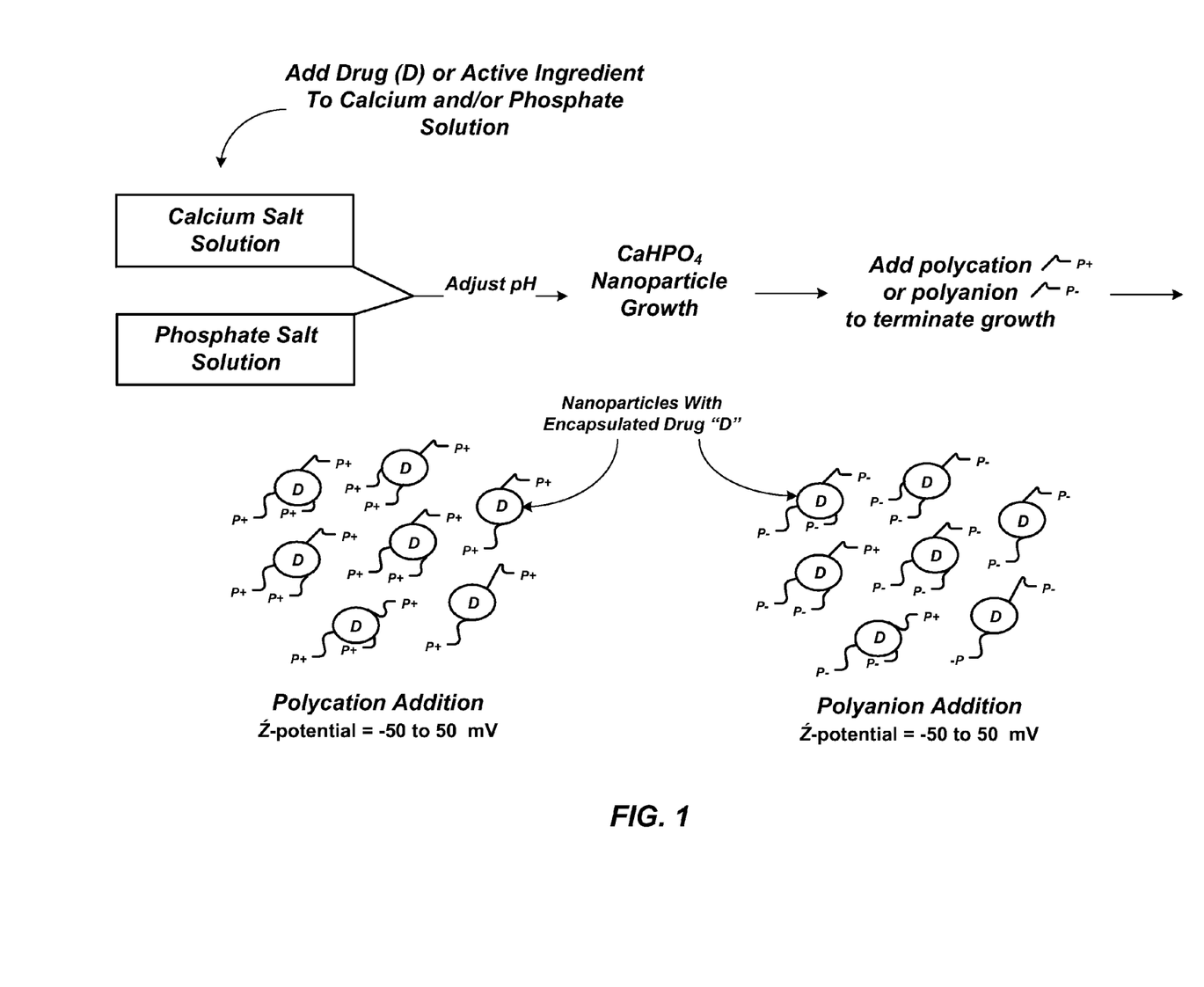
FIG. 1 illustrates one example of a generally non-aggregating nanoparticle containing an encapsulated drug or other active ingredient.

Attention is next directed to FIG. 1, while illustrates one exemplary embodiment for the formation of a generally non-aggregating nanoparticle containing a drug or any other selected ingredient for encapsulation within the nanoparticle and/or which drug or active ingredient may be associated with the nanoparticle through some form of electrostatic association. As can be seen, an aqueous calcium salt solution ($CaCl_2$) may be prepared along with an aqueous phosphate salt ($Na_2PO_4$) solution. A drug (D) or other active ingredient may be added to one or both of these aqueous based salt solutions, which may then be followed by pH adjustment. Accordingly, while FIG. 1 illustrates the use of a drug "D", to facilitate an understanding of the current invention, it can be appreciated that any sort of active ingredient may be used in any of the various embodiments of the present disclosure. Accordingly, an active ingredient herein may be understood as any chemical (e.g. a chemical compound that may be isolated or synthesized) or biological molecule (e.g. a compound formed in a living plant or organism) that may be encapsulated and/or associated with the nanoparticles. A pharmaceutically active ingredient may be understood herein as any ingredient that may be selected and administered to a patient, utilizing the nanoparticles disclosed herein, which ingredient is pharmacologically active and capable of providing a therapeutic effect to a person or animal.

More specifically, the drug or pharmaceutically active ingredient may be dissolved in a common solvent for the above referenced aqueous salt solutions and active ingredient. For example, a water/acetone and/or water/alcohol solution may be employed. The drug or active ingredient may therefore be hydrophobic and capable of dissolving in an organic solvent, and/or a hydrophilic drug or active ingredient capable of water absorption and/or being dissolved in water. The drug or active ingredient may also be a charged drug or active ingredient molecule having a net electrostatic charge or net dipole, or as noted more fully below, be capable of a hydrogen bond type interaction.

The pH may then be specifically be adjusted to a value of greater than 7.0, e.g. the pH may be adjusted to a value of about 8.0. For example, it has been found that at a pH of about 8.0, the ensuing nanoparticles may be formed with a largest dimension of about 200 nm. The size of the nanoparticles so formed has also been found to increase with increasing pH, and at a pH of about 10 the particle size approaches the level of about 1 micron. Accordingly, one may specifically combine a calcium salt such as calcium chloride ($CaCl_2$) with salt of phosphoric acid such as sodium hydrophosphate ($Na_2HPO_4$) and form $CaHPO_4$ according to the following general equation:

$CaCl_2.2H_2O+Na_2HPO_4 \rightarrow CaHPO_4.2H_2O+2NaCl$

As can also be seen in FIG. 1, upon addition of either a polycation (~P+) or polyanion (~P−), the growth of the particles, now containing an encapsulated drug or active ingredient, may be terminated. Reference to either a polycation or polyanion herein may be understood as reference to a polymeric component that provides either a net cationic or anionic type charge. In addition, such polymeric components may have a number average molecular weight (Mn) value of 100-30,000, including all values and increments therein. The value of Mn may therefore advantageously be selected such that the corresponding polycation or polyanion may absorb onto the surface of the nanoparticles, but not be so high that the nanoparticles might bridge (i.e. agglomerate due to entanglement of the polymeric chains of the polycation or polyanion component).

Upon addition of either the polycation or polyanion, the nanoparticles that are formed are such that they are generally non-aggregating, i.e. they indicate a reduced agglomeration as compared to non-charged nanoparticles due to their net charging characteristics. The polycationic or polyanionic polymer may therefore be added from a 50% solution by weight containing the polycationic or polyanionic polymer, which solution may be introduced at a level of 0.05%-10.0% by volume for a given volume of the salt solutions. Accordingly, the polycationic or polyanionic polymer may be introduced at a level of 0.05% to 5.0% by volume for a given volume of salt solution. More specifically, the nanoparticles are such that they are provided with a zeta potential (Ź-potential) of −50 to 50 millivolts (mV), including all values and increments therein. It should also be noted that at least one method for determining the Ź-potential is to apply an electric field across the particles within a dispersion and particles with a given Ź-potential will migrate toward the electrode of opposite charge with a velocity proportional to the magnitude of the Ź-potential. The velocity may be measured using the technique of Laser Doppler Anemometer. The frequency shift or phase shift of an incident laser beam caused by the moving particles is measured as the particle mobility, and such mobility is converted to the Ź-potential by inputting the dispersant viscosity and then calculating the Ź-potential. The Ź-potential herein was measured utilizing a Zetapals instrument available from Brookhaven Instrument Corporation.

In addition, the generally non-aggregating characteristics of the nanoparticles herein are such that they may be isolated and nonetheless resuspended in a given liquid medium, while maintaining their non-aggregating characteristics. For example, the nanoparticles may be stored for a period of time (e.g. not in a given liquid) such as up to about 8 weeks at ambient temperatures, and then resuspended in a liquid, at which point their non-aggregating characteristics still remain available for use in a manner as disclosed herein.

Expanding upon all of the above, the particular polycations (~P+) as suitable herein may include any polymeric type molecule that is capable of providing a net cationic charge to the nanoparticles to, as noted, reduce nanoparticle agglomeration. Such cationic charge may therefore be present on a main polymer chain and/or on a side-chain, where a side chain may be understood as itself having a molecular weight or degree of polymerization that is less than the main chain from which it extends. For example, one may employ polyethyleneimine (PEI), polyamines, polylysine (e.g. having 25~30 L-Lysine repeating units), and/or cationic oligopeptide polymers. Again, any of these polymers may have a Mn value of $\leqq 30,000$, as noted above. Oligopeptides may specifically be understood as macromolecules containing between two to twelve amino acid (AA) repeating units. Other suitable polycations may include polyarginine, protamines and diethylaminoethyl-dextran (DEAE-dextran).

The polyethylene imine may itself also specifically amount to a branched polymer with about 25% primary amine groups, 50% secondary amine groups and 25% tertiary amine groups, thereby having the formula:

wherein x and y are integers that may be adjusted to provide the relative proportion of primary amine groups and secondary amine groups that may be desired, and the value of n may be adjusted to provide an overall number average molecular weight of $\leqq 30,000$.

With respect to polyanions (~P−) such may similarly include any type of polymeric molecule that is capable of providing a net negative charge to the nanoparticles to similarly reduce nanoparticle agglomerations. Suitable polyanions may therefore include polyacrylic acid (PAA), polyglutaminc acid, and/or anionic oligopeptide polymers (having molecular weights of $\leqq 10,000$). Other suitable polyanions may include poly(aspartic acid), polyethyleneglycol-b-poly(aspartic acid) copolymer and polypropylacrylic acid.

Furthermore, with respect to either the polycationic or polyanionic type polymers disclosed herein, such polymers may also be prepared with a controlled charged content by selective copolymerization with an otherwise non-charged monomer. For example, in the case of polyacrylic acid, which may serve to supply a selected amount of anionic charge, one may copolymerize with ethylene to thereby reduce the relative amount of net charge on the polymer chain. Accordingly, one may position the particular anion and/or cationic charge on less than 100% of the repeating units, and it is contemplated herein that such charge may be installed on 1-99% of the repeating units, including all values and increments herein.

Figure 2:
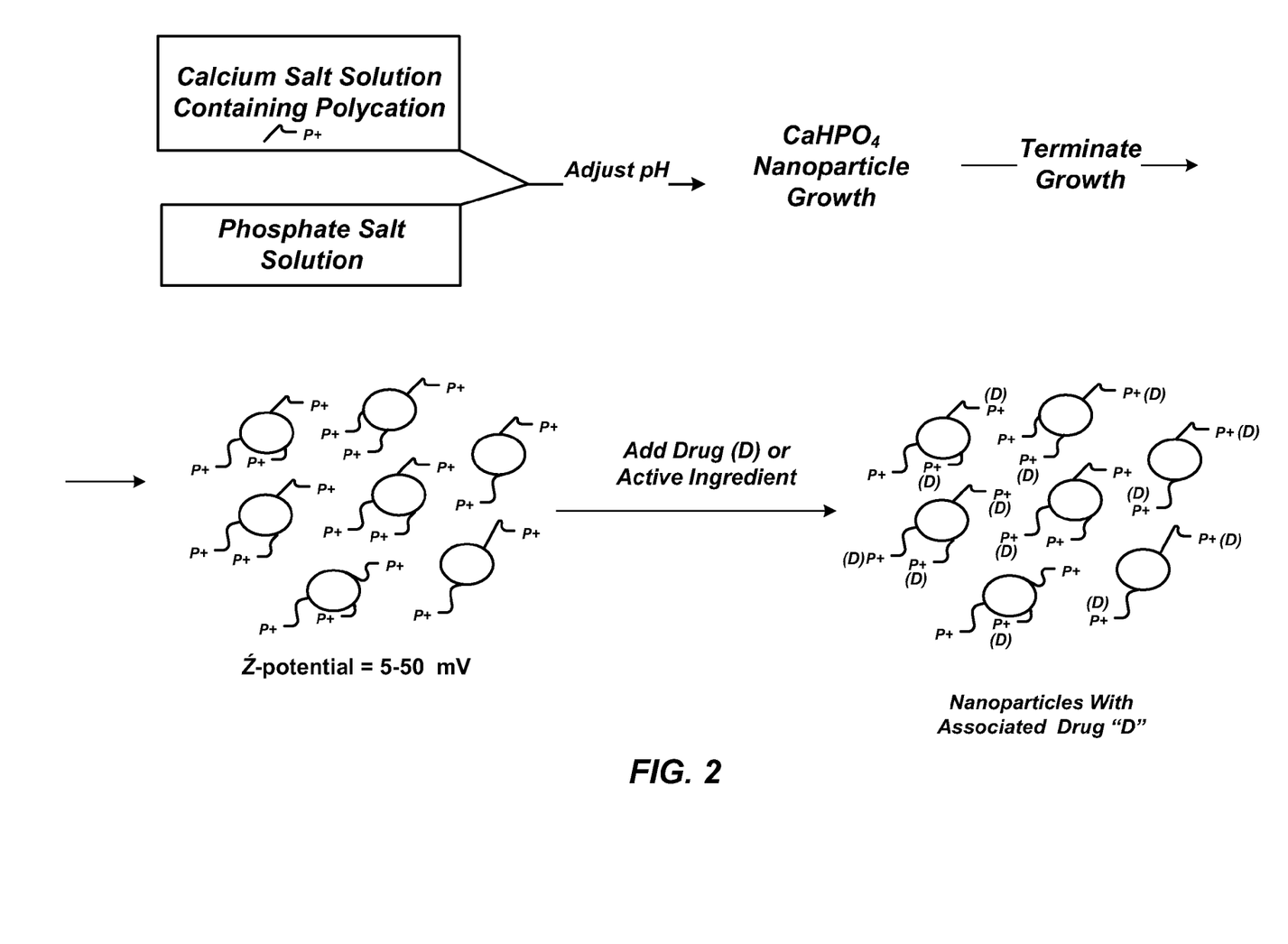
FIG. 2 illustrates another example of a generally non-aggregating nanoparticle, with a cationic charge, along with an associated drug or other active ingredient.

Attention is next directed to FIG. 2, which illustrates another embodiment of the present invention. In this embodiment, one may form a net electrostatic charge on the surface of the nanoparticle, which net electrostatic charge may then be employed to generally avoid particle agglomeration as well as providing a site for drug or active ingredient association. As noted above, this may be developed by regulating the Ź-potential to a level of −50 to 50 millivolts (mV), which in turn may be accomplished by regulating the amount of polycation that is employed during the nanoparticle preparation. Accordingly, in this embodiment, the drug and/or pharmaceutically active ingredient may therefore be associated with the nanoparticle surface, as opposed to being encapsulated in the solid phase of the particle, as described above. In this procedure one may therefore utilize a drug or pharmaceutically active ingredient that is capable of electrostatic association with the net charge on the nanoparticle surface. As alluded to above, such electrostatic association may in turn amount to a secondary bonding interaction (i.e. any sort of bonding interaction other than a covalent bond) such as hydrogen bonding, a dipole-dipole interactions, and/or it may also rely upon van der Waals type forces.

It may therefore be appreciated that associating the active ingredient via the electrostatic association noted above, may serve to increase the stability of the nanoparticles, thermodynamically, against agglomeration. That is, the method herein may be understood as a method to increase the relative thermal stability of a charged, ionizable or hydrogen-bonding active ingredient through association with the nanoparticles described herein, wherein the relative increase in thermal stability may occur by charge-balancing as between the nanoparticle and the active ingredient.

The generally non-aggregating nanoparticles herein, aside from being characterized with the above referenced Ź-potential values, may also be understood as nanoparticles which, when suspended in a given liquid, are such that 50% or more of the nanoparticles remain suspended after a period of time of up to and including 120 hours (e.g. the particles do not settle and aggregate as a layer). Accordingly, in the context of the present disclosure, the generally non-aggregating nanoparticles may be understood as nanoparticles wherein 50% to 100% of such particles are capable of remaining suspended in a given liquid medium, for a period of time up to and including 120 hours. For example, 50% of the nanoparticles may remain suspended over the entire 120 hour period, or 55% remain suspended, or 60% remain suspended, or 65% remain suspended, or 70% remain suspended, etc., up to 100% of the particles remaining suspended, after 120 hours.

More specifically now, as illustrated in FIG. 2, one may combine a salt solution containing a polycation with the phosphate salt solution, adjust pH to a level above 7.0 but less than or equal to about 10, to provide for $CaHPO_4$ nanoparticle growth. Nanoparticle growth may then be terminated, which may be achieved by the addition of a sufficient amount of anionic component, such as one or more of the polyanionic polymers noted above. The solution containing the nanoparticles may then be stirred for a selected time period (e.g. 30 minutes) at which point a drug and/or active ingredient, for association with the charged nanoparticle surface, may be added.

Figure 3:
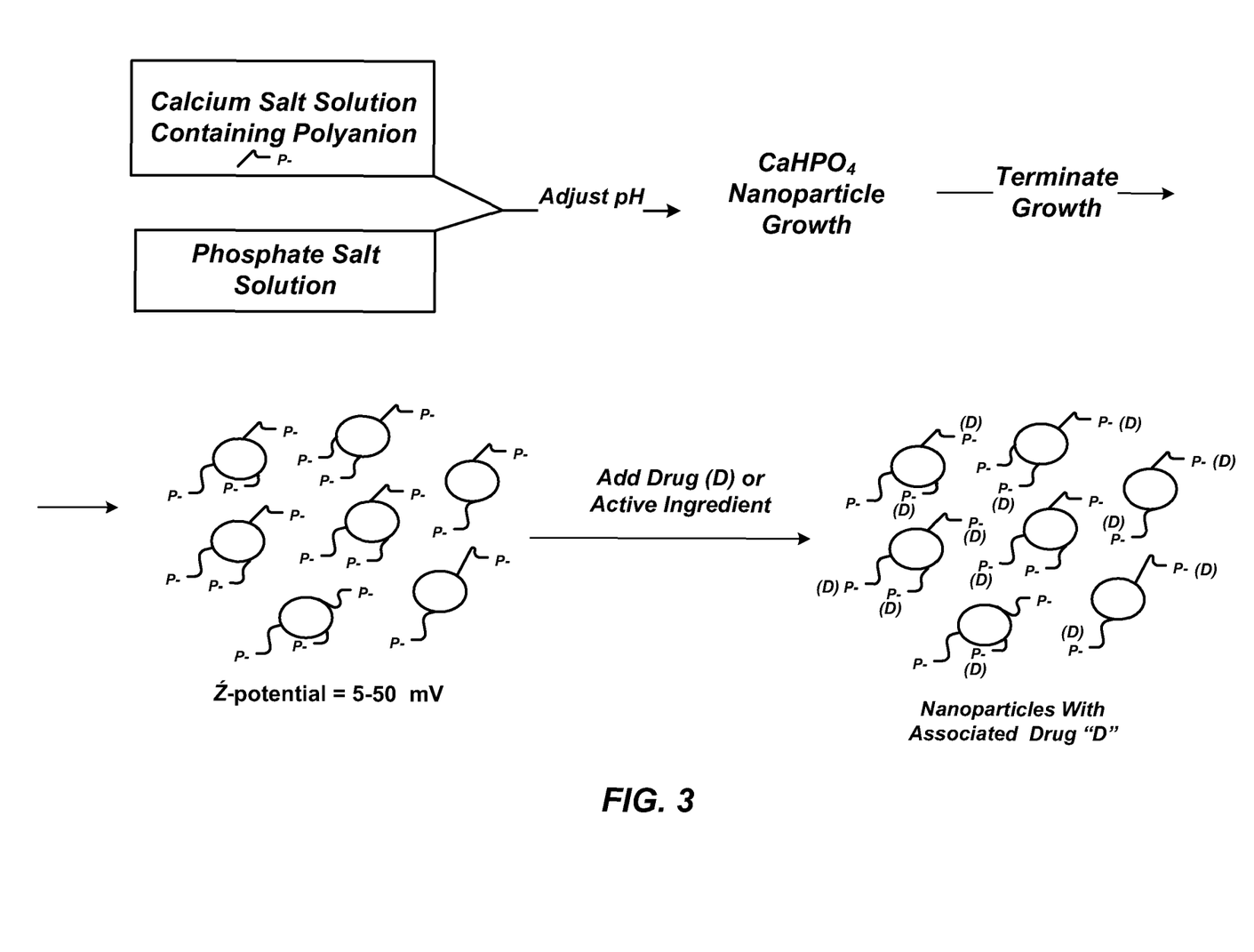
FIG. 3 illustrates another example of a generally non-aggregating nanoparticle, with an anionic charge, along with an associated drug or other active ingredient.

As may therefore be appreciated, and with attention directed to FIG. 3, it is contemplated that one may also combine a salt solution containing a polyanion with the phosphate salt solution, adjust pH to a level above 7.0 and less than or equal to about 10, to provide for $CaHPO_4$ nanoparticle growth. Nanoparticle growth may then be terminated, which may be achieved by the addition of a sufficient amount of cationic component, such as one or more of the polycationic polymers noted above. The solution containing the nanoparticles may then be stirred for a selected time period (e.g. 30 minutes) at which point a drug and/or active ingredient, for association with the anionic charged nanoparticle surface, may again be added.

Figure 4A:
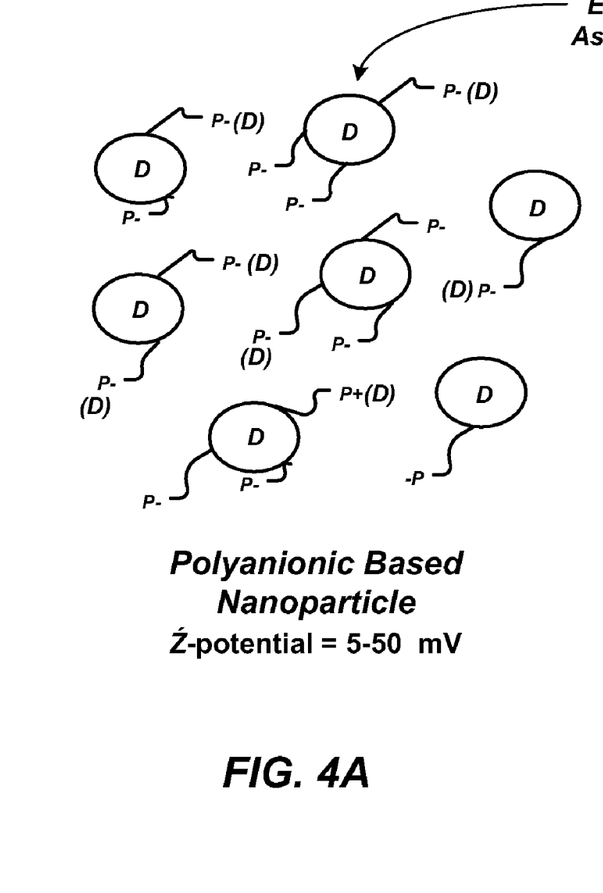
FIG. 4A illustrates a polyanionic based generally non-aggregating nanoparticle, containing an encapsulated drug or other active ingredient, as well as an associated drug or active ingredient.
Figure 4B:
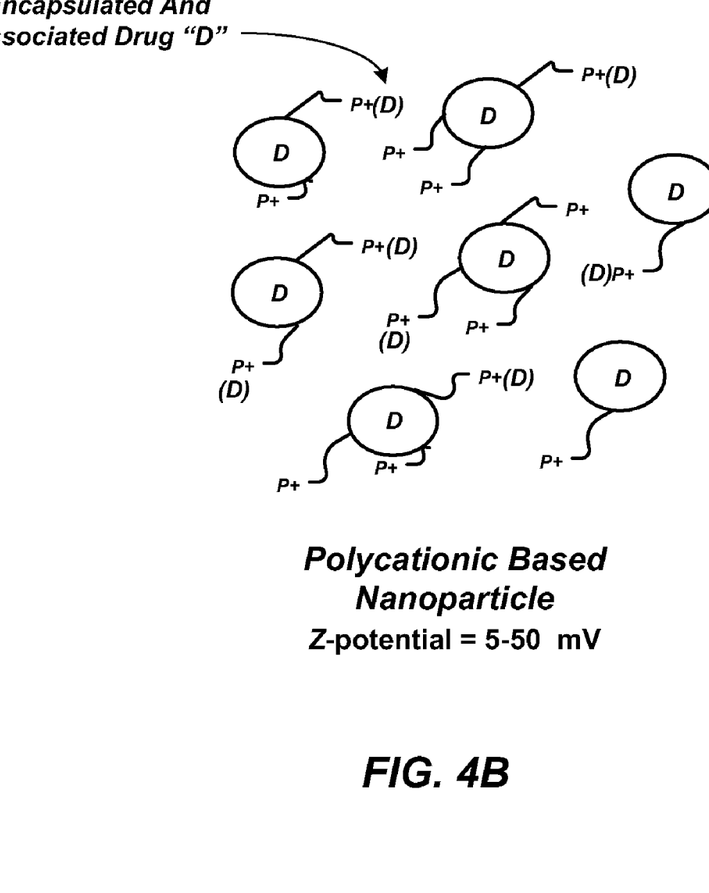
FIG. 4B illustrates a polycationic based generally non-aggregating nanoparticle, containing an encapsulated drug or other active ingredient, as well as an associated drug of active ingredient.

In addition, attention is next directed to FIG. 4A and FIG. 4B, which illustrates that one may prepare nanoparticles herein that include both an embedded drug or pharmaceutically active ingredient, as well as a selected amount of a drug or pharmaceutically active ingredient associated with the charged surface. In FIG. 4A, one may therefore utilize the cationic form for the charged nanoparticles, and in FIG. 4B, one may use the anionic form. Accordingly, it may be appreciated that one may also embed into the nanoparticles a first type of drug or pharmaceutically active ingredient and then associate on the surface of the nanoparticles a second and different drug or pharmaceutically active ingredient, where each active ingredient may therefore provide differing therapeutic effects.

Accordingly, it may again be appreciated that the present disclosure provides the ability to increase the thermal stability of charged materials (e.g. a charged active ingredient) through association with a charged nanoparticle. The particular active ingredients that may be embedded and/or associated with the nanoparticles herein, may include biological compounds such as DNA and/or single or double stranded RNA sequences, used for RNA interference or silencing. In addition, the active ingredients may include protein molecules, including but not limited to human growth hormone, insulin or salmon calcitonin, or hyaluronidase, carnosine and/or exenetide. In that regard that active ingredient may include antigens or those substances which can be recognized by the adaptive immune systems or which can prompt the generation of antibodies and cause an immune response. Other active ingredients may include psychoactive drugs (e.g. benzodiazepines), alkaloids and/or various heterocyclic compounds, such as 5-fluorouridine or 5-fluorouracil. The active ingredient may also include muscarinics such as atropine. In addition, one may associate hydrophobic molecules with the charged nanoparticles herein, one example of which may include the use of the carboxylic acid moiety on Vitamin A.

EXAMPLES

Example 1

Figure 5:
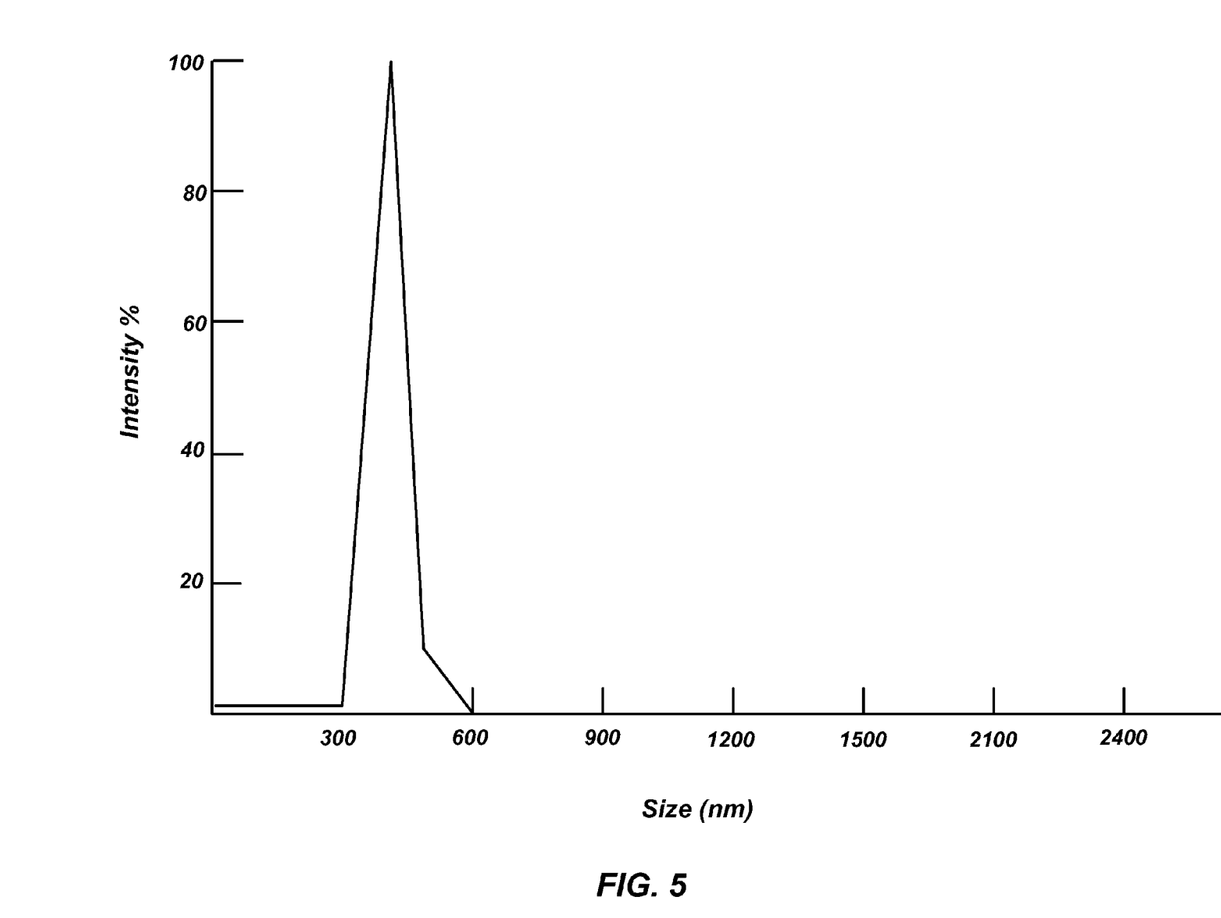
FIG. 5 is a plot of the size range distribution for the nanoparticles prepared in accordance with Example 1.

Nanoparticle Preparation Containing Polycationic Polymer on the Nanoparticle Surface Equal volume of 250 mM calcium chloride solution and 2.5 mM sodium phosphate tribasic solution were mixed. The pH values of both solutions were adjusted to 8.0 using 1N NaOH prior to mixing. To the mixture, a 2% (v/v) of a 50% polyethylenimine solution was added. Calcium phosphate nanoparticles with particle sizes of 380 nm (zeta potential 8 mV) were obtained. FIG. 5 illustrates the size range distribution for the particles prepared according to this procedure. The data in FIG. 5, as well all other particle size data reported herein, was conveniently generated by a Beckman Coulter N4 Plus particle analyzer, which indicates an average numerical particle size for a given sample via light scattering techniques.

Example 2

Hydrophobic Drug Molecule Encapsulation in Nanoparticles

Figure 6:
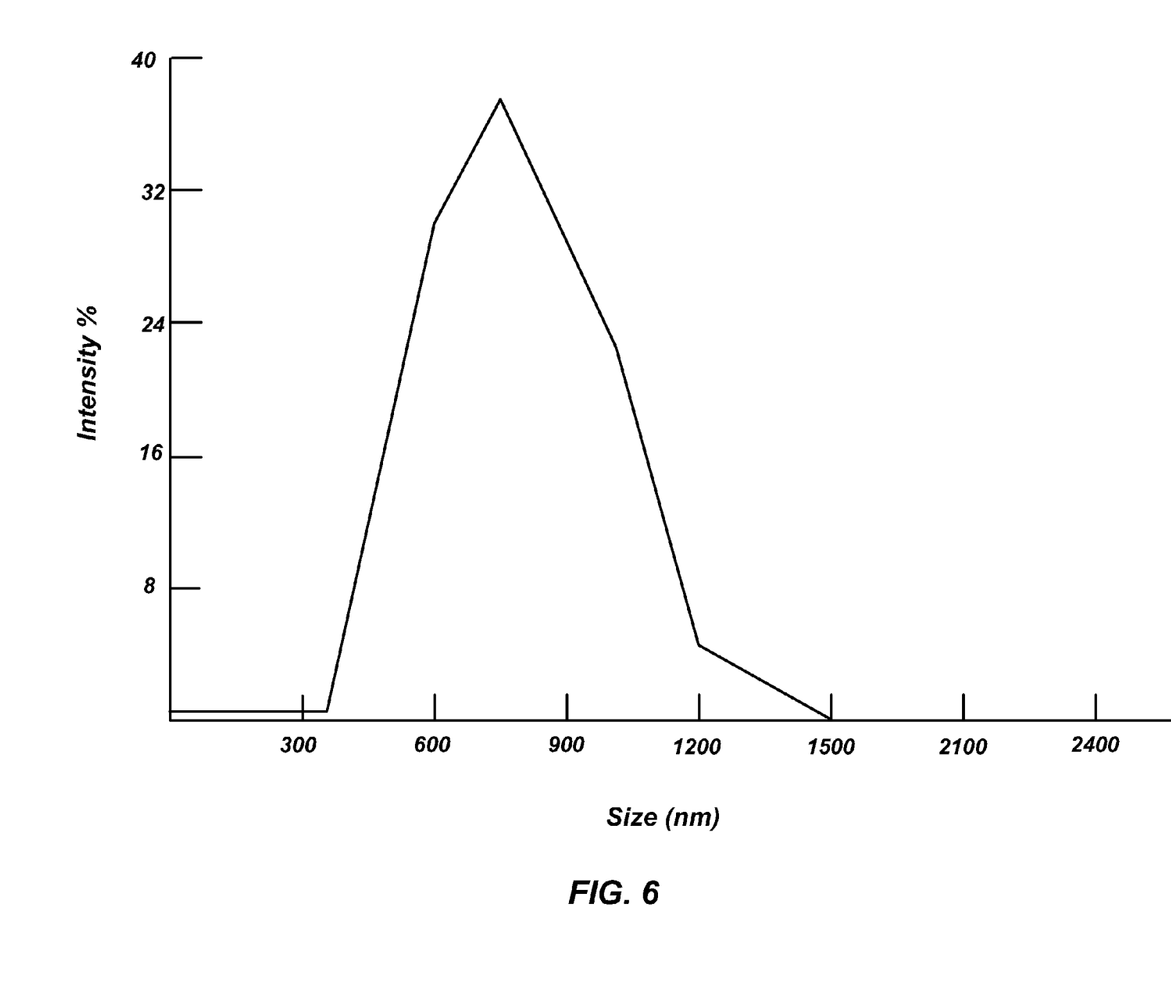
FIG. 6 is a plot of the size range distribution for the nanoparticles prepared according to Example 2.

Midazolam (free base), also known as 8-chloro-6-(2-fluorophenyl)-1-methyl-4H-imidazo[1,5-a][1,4]benzodiazepine, was used as an example of a hydrophobic active pharmaceutical ingredient (API) for use in combination of the nanoparticles of the present disclosure. Accordingly, an acetone solution of midazolam at 2 mg/mL concentration was mixed with the calcium chloride solution prior to addition to the phosphate solution following Example 1 above. Calcium phosphate encapsulated midazolam was obtained as 740 nm particles with a zeta potential of 8 mV. FIG. 6 illustrates the size range distribution for the encapsulated midazolam nanoparticles prepared according to this procedure.

Example 3

Nanoparticle Preparation Containing Polycationic Polymer on the Nanoparticle Surface Equal volume of 6.25 mM calcium nitrate solution containing 0.10% (v/v) of a 50% polyethylenimine solution and 3.74 mM ammonium phosphate solution were mixed. The pH values of both solutions were adjusted to 8.0 using 1N NaOH prior to mixing. To the mixture a 0.03% (v/v) of 4.5% poly (acrylic acid) solution was added. Calcium phosphate nanoparticles with an average particle size of 180 nm were obtained, zeta potential −37 mV.

Example 4

Hydrophilic drug Molecule Encapsulation in Calcium Phosphate Nanoparticles

Figure 7:
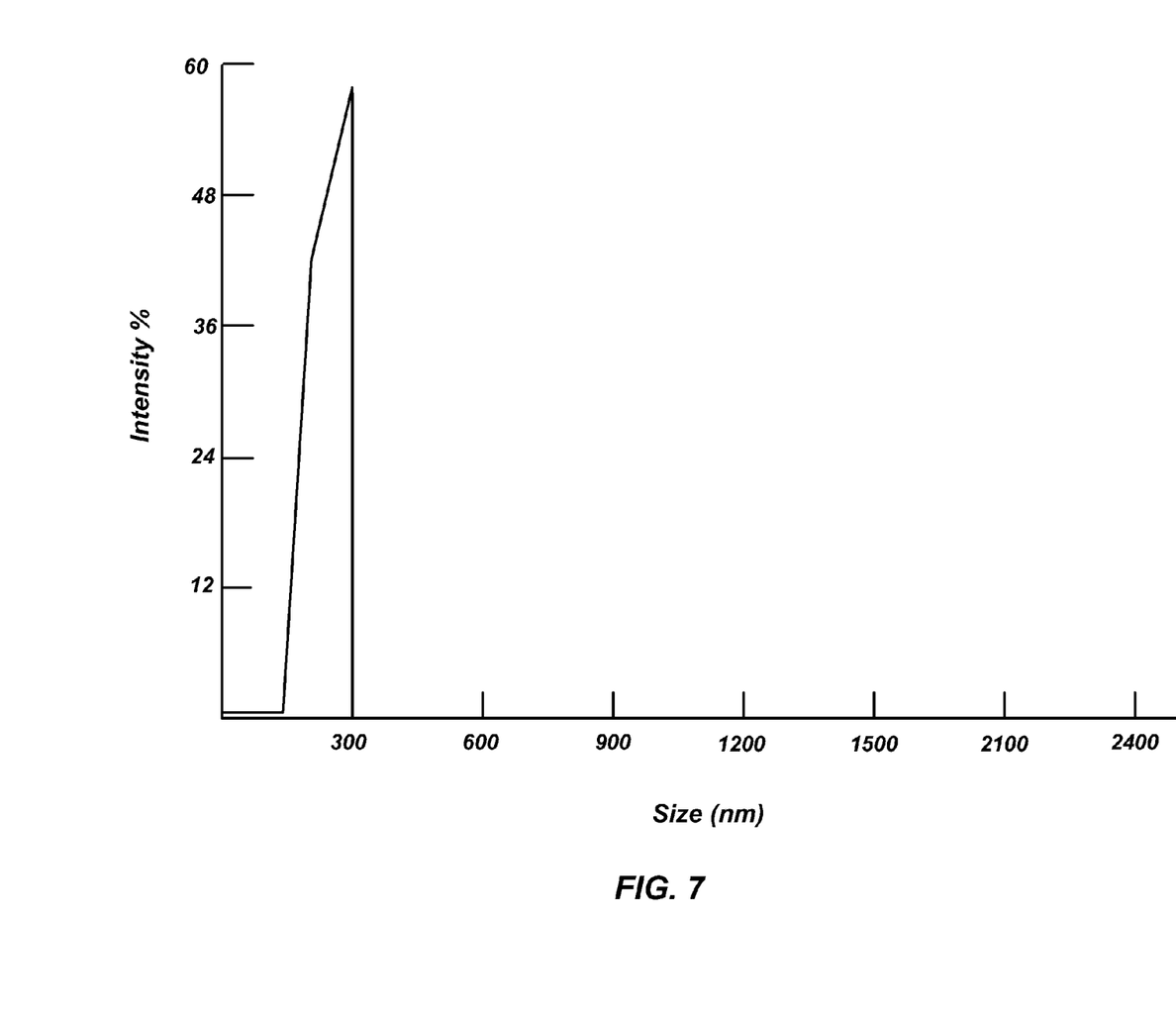
FIG. 7 is a plot of the size range distribution for nanoparticles containing encapsulated sodium fluorescein.
Figure 8:
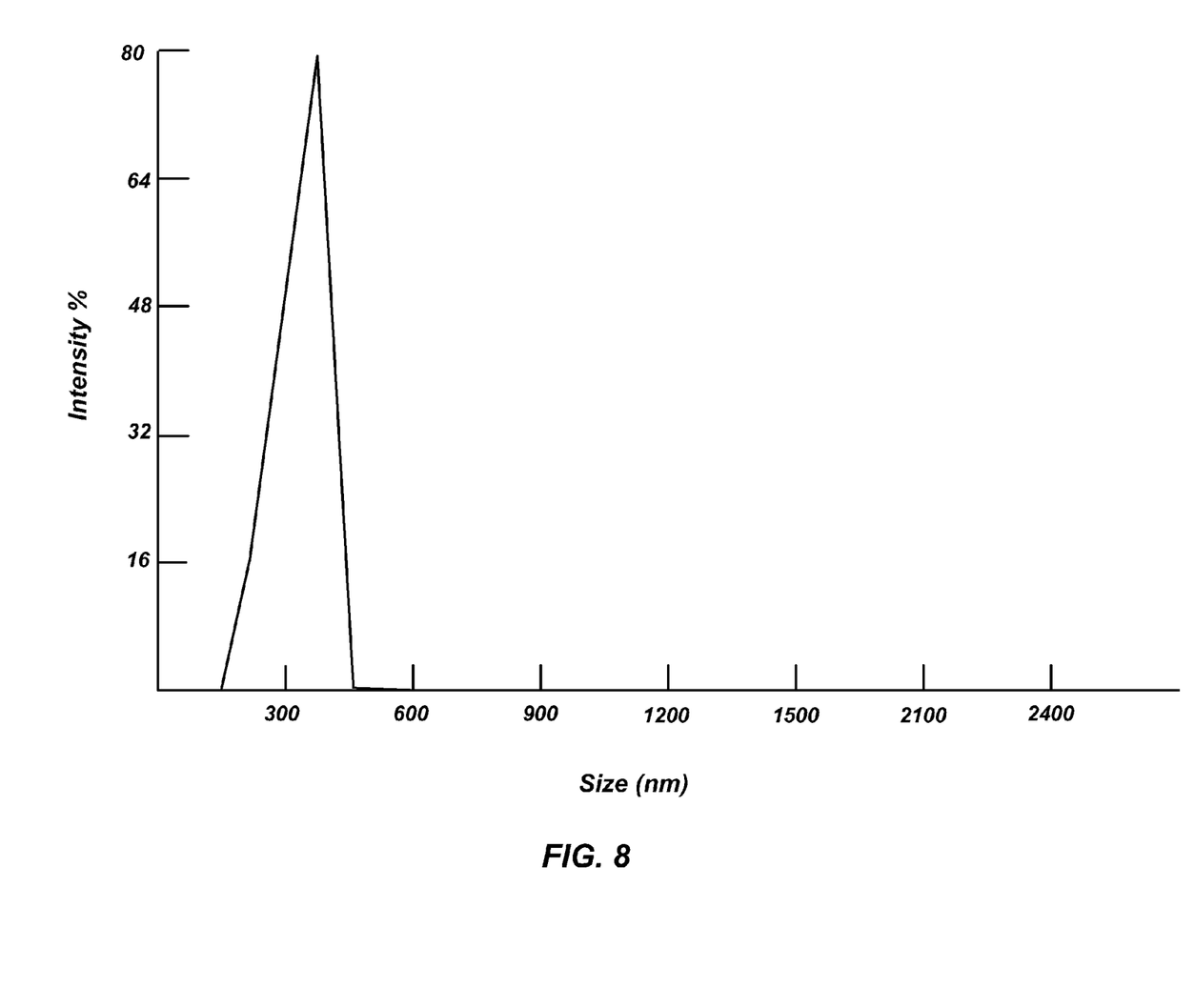
FIG. 8 is a plot of the size range distribution for nanoparticles containing encapsulated sodium fluorescein, after 120 hours.

Sodium fluorescein ($C_{20}H_{10}O_5Na_2$) was used as an example of a hydrophilic ingredient for use in the nanoparticles of the present disclosure. Accordingly, sodium fluorescein was incorporated in the phosphate solutions (at 3.3 µg/mL concentration). The procedure in Example 3 was then followed and calcium phosphate nanoparticles containing encapsulated sodium fluorescein was obtained as 217 nm particles with a zeta potential of 27 mV (FIG. 7). These calcium phosphate/fluorescein nanoparticles are stable and do not aggregate, as demonstrated by FIG. 8, which indicates the particle size distribution of the calcium phosphate particles stored at room temperature for 120 hours. As can be seen, the particle size distribution for the nanoparticles was initially in the range of about 150-300 nm, and as can be observed, after 120 hours, the nanoparticles are measured to indicate a size in the range of about 150-400 nm, which is one example of their generally non-aggregating characteristics. In addition, these generally non-aggregating fluorescent-labeled calcium phosphate nanoparticles were then shown as efficient carriers for cellular delivery in HeLa cells.

It may now be appreciated that the present disclosure provides the ability to encapsulate or absorb a wide variety of actives (drugs) of various charge and hydrophilicity with bioresorbable calcium phosphate (CaP) nanoparticles of sufficient zeta potential (≧5 mV) to control agglomeration of the nanoparticles over time. In addition, the present disclosure identifies that one may bind a drug or other active ingredient to the inorganic nanoparticles so that such drug or active ingredient is not prematurely released before endocytosis into or absorption onto target cells or bio-structural components (e.g. bone or skeletal structure).

Example 5

Resuspendable CaP Nanoparticle Containing Polyanionic Polymer on the Nanoparticle Surface Aqueous solutions of calcium chloride (200 mM) and sodium phosphate (267mM) were mixed at a 2:1 volume ratio. To the mixture a 0.2% (v/v) of 45% poly(acrylic acid) solution was added. Calcium phosphate nanoparticles with an average size of 268 nm and a zeta potential of −42 mv. After purification by centrifugation, the nanoparticles were lyophilized. The lyophilized nanoparticles were able to be resuspended (which may be aided with sonification) and behaved in a non-aggregating manner, as disclosed herein, in deionized water after 7 weeks at ambient temperature.

What is claimed is:

1. A method for preparing non-aggregating calcium phosphate nanoparticles comprising:
    (a) adding an active ingredient to one of a calcium salt solution or a phosphoric acid salt solution;
    (b) forming a mixed solution by mixing said calcium salt solution with said phosphoric acid salt solution;
    (c) adjusting the pH of said mixed solution to a level greater than 7.0 and less than or equal to 10.0, thereby forming calcium phosphate nanoparticles;
    (d) terminating the formation of said calcium phosphate nanoparticles by adding a polycation and/or polyanion to said mixed solution, wherein said polycation or polyanion has a number average molecular weight (Mn) of 100-30,000 and is added from a solution containing said polycation or polyanion, said solution containing said polycation or polyanion being added at a level of 0.05%-10.0% by volume of said mixed solution.

2. The method of claim 1 wherein said calcium phosphate nanoparticles have a zeta potential of −50 to 50 millivolts.

3. The method of claim 1 wherein the formation of said calcium phosphate nanoparticles is terminated by adding said polycation to said mixed solution, said polycation comprising a polymeric type molecule having a main chain and a side chain, wherein one of said main chain or side chain contains a net cationic charge.

4. The method of claim 1 wherein the formation of said calcium phosphate nanoparticles is terminated by adding said polycation to said mixed solution, said polycation comprising poly(ethylene imine) having a number average molecular weight of less than or equal to 30,000.

5. The method of claim 4 wherein said poly(ethylene imine) has the following structure:

where x and y are integers and the value of n is adjusted to provide for a number average molecular weight of less than or equal to 30,000.

6. The method of claim 1 wherein the formation of said calcium phosphate nanoparticles is terminated by adding said polycation to said mixed solution, and said polycation is selected from the group consisting of polyamines, polylysine, oligopeptides, polyarginine, protamines and diethylaminoethyl-dextran.

7. The method of claim 1 wherein the formation of said calcium phosphate nanoparticles is terminated by adding said polyanion to said mixed solution, and said polyanion is selected from the group consisting of polyacrylic acid, polyglutamic acid, oligopeptides, poly(aspartic acid), polyethyleneglycol-b-poly(aspartic acid) copolymer and polypropylacrylic acid.

8. The method of claim 1, wherein when said calcium phosphate nanoparticles are suspended in a liquid medium, 50% or more of said calcium phosphate nanoparticles remain suspended after a time period of 120 hours.

9. The method of claim 1, wherein said active ingredient comprises a pharmaceutical active ingredient.

10. The method of claim 1 wherein the formation of said calcium phosphate nanoparticles is terminated by adding said polycation comprising poly (ethylene imine) to said mixed solution, and said active ingredient comprises midazolam.

11. The method of claim 1 wherein said active ingredient is encapsulated in said calcium phosphate nanoparticles.

12. The method of claim 1 wherein said calcium phosphate nanoparticles have a size range of 1 nm to 999 nm.

13. The method of claim 1 wherein said calcium phosphate nanoparticles have a size range of 50 nm to 400 nm.

14. The method of claim 1 wherein said calcium phosphate nanoparticles have a size range of 100 nm to 300 nm.

15. The method of claim 1 wherein said calcium phosphate nanoparticles have a size range of 190 nm to 210 nm.

16. A method for preparing non-aggregating calcium phosphate nanoparticles comprising:
(a) forming a mixed solution by mixing a solution of a calcium salt with a phosphoric acid salt solution;
(b) adjusting the pH of said mixed solution to a level greater than 7.0 and less than or equal to 10.0, thereby forming calcium phosphate nanoparticles;
(c) terminating the formation of said calcium phosphate nanoparticles by adding a polycation and/or polyanion to said mixed solution wherein said polycation or polyanion has a number average molecular weight (Mn) of 100-30,000 and is added from a solution containing said polycation or polyanion, said solution of polycation or polyanion being added at a level of 0.1-10.0% by volume of said mixed solution;
(d) adding an active ingredient to said calcium phosphate nanoparticles wherein said active ingredient is associated with a surface of one or more of said calcium phosphate nanoparticles via a secondary bonding interaction.

17. The method of claim 16 wherein said calcium phosphate nanoparticles have a zeta potential of −50 to 50 millivolts.

18. The method of claim 16 wherein formation of said calcium phosphate nanoparticles is terminated by adding said polycation to said mixed solution, said polycation comprising a polymeric type molecule having a main chain and a side chain, wherein one of said main chain or side chain contains a net cationic charge.

19. The method of claim 16 wherein formation of said calcium phosphate nanoparticles is terminated by adding said polycation to said mixed solution, said polycation comprising poly(ethylene imine) having a number average molecular weight of less than or equal to 30,000.

20. The method of claim 19 wherein said poly(ethylene imine) has the following structure:

where x and y are integers and the value of n is adjusted to provide for a number average molecular weight of less than or equal to 30,000.

21. The method of claim 16 wherein formation of said calcium phosphate nanoparticles is terminated by adding said polycation to said mixed solution, and said polycation is selected from the group consisting of polyamines, polylysine, oligopeptides, polyarginine, protamines and diethylaminoethyl-dextran.

22. The method of claim 12 wherein formation of said calcium phosphate nanoparticles is terminated by adding said polyanion to said mixed solution, and said polyanion is selected from the group consisting of polyacrylic acid, polyglutamic acid, oligopeptides, poly(aspartic acid), polyethyleneglycol-b-poly(aspartic acid) copolymer and polypropylacrylic acid.

23. The method of claim 16, wherein when said calcium phosphate nanoparticles are suspended in a liquid medium, 50% or more of said calcium phosphate nanoparticles remain suspended after a time period of 120 hours.

24. The method of claim 16, wherein said active ingredient comprises a pharmaceutical active ingredient.

25. The method of claim 16 wherein formation of said calcium phosphate nanoparticles is terminated by adding said polycation to said mixed solution, said polycation comprises poly (ethylene imine) and said active ingredient comprises midazolam.

26. The method of claim 16 wherein said calcium phosphate nanoparticles have a size range of 1 nm to 999 nm.

* * * * *